(12) United States Patent
Chowdhury

(10) Patent No.: US 7,891,235 B2
(45) Date of Patent: Feb. 22, 2011

(54) METHOD FOR MONITORING WATER QUALITY

(75) Inventor: Sudhir Chowdhury, Farsta (SE)

(73) Assignee: Predect AB, Stockholm (SE)

(*) Notice: Subject to any disclaimer, the term of this patent is extended or adjusted under 35 U.S.C. 154(b) by 34 days.

(21) Appl. No.: 12/090,076

(22) PCT Filed: Nov. 10, 2006

(86) PCT No.: PCT/US2006/060760

§ 371 (c)(1),
(2), (4) Date: Apr. 11, 2008

(87) PCT Pub. No.: WO2007/100390

PCT Pub. Date: Sep. 7, 2007

(65) Prior Publication Data

US 2008/0289402 A1 Nov. 27, 2008

Related U.S. Application Data

(60) Provisional application No. 60/736,343, filed on Nov. 14, 2005.

(51) Int. Cl.
G01N 15/06 (2006.01)
G01N 1/20 (2006.01)

(52) U.S. Cl. ................... 73/61.71; 73/863.01

(58) Field of Classification Search ............. 73/61.71, 73/53.01, 865.5, 53.07, 61.42, 863.01; 356/335; 210/85

See application file for complete search history.

(56) References Cited

U.S. PATENT DOCUMENTS

| | | | | |
|---|---|---|---|---|
| 3,233,173 A | * | 2/1966 | Kleinschmidt et al. | 324/663 |
| 3,710,615 A | * | 1/1973 | Johnson et al. | 73/61.75 |
| 3,719,090 A | * | 3/1973 | Hathaway | 73/865.5 |
| 3,816,773 A | * | 6/1974 | Baldwin et al. | 310/319 |
| 3,897,687 A | | 8/1975 | Burberry | |
| 4,015,464 A | * | 4/1977 | Miller et al. | 73/61.75 |
| 4,381,674 A | * | 5/1983 | Abts | 73/599 |
| 4,587,518 A | * | 5/1986 | King | 340/603 |
| 4,628,748 A | * | 12/1986 | Jogan et al. | 73/863.01 |
| 4,660,422 A | | 4/1987 | Eads et al. | |
| 4,674,337 A | * | 6/1987 | Jonas | 73/861.73 |
| 4,685,066 A | * | 8/1987 | Hafele et al. | 702/50 |
| 4,765,963 A | * | 8/1988 | Mukogawa et al. | 422/68.1 |
| 5,091,863 A | * | 2/1992 | Hungerford et al. | 700/283 |
| 5,299,141 A | * | 3/1994 | Hungerford et al. | 702/49 |
| 5,377,005 A | * | 12/1994 | Meyer | 356/335 |
| 5,435,909 A | * | 7/1995 | Burrows | 210/85 |
| 5,616,870 A | * | 4/1997 | Bowen et al. | 73/863.01 |

(Continued)

FOREIGN PATENT DOCUMENTS

WO   2005/022145   3/2005

(Continued)

*Primary Examiner*—John Fitzgerald
(74) *Attorney, Agent, or Firm*—Fasth Law Offices; Rolf Fasth

(57) ABSTRACT

The method is for monitoring water quality in a water system. A water pipe is provided for conveying water therein. A particle sensor is in operative engagement with the water pipe. The particle sensor continuously counts particles in the water of the water pipe. The particle sensor triggers the taking of a water sample only when the particle count reaches a predetermined level.

18 Claims, 3 Drawing Sheets

U.S. PATENT DOCUMENTS

| | | | | |
|---|---|---|---|---|
| 5,619,333 | A * | 4/1997 | Staff et al. | 356/436 |
| 5,646,863 | A | 7/1997 | Morton | |
| 5,668,309 | A * | 9/1997 | Codina et al. | 73/61.71 |
| 5,730,942 | A * | 3/1998 | Megerle et al. | 422/82.01 |
| 5,870,692 | A * | 2/1999 | Millo | 702/45 |
| 6,245,224 | B1 | 6/2001 | Enoki et al. | |
| 6,491,872 | B1 * | 12/2002 | Wick | 422/72 |
| 6,658,876 | B1 | 12/2003 | Richardson et al. | |
| 6,753,186 | B2 * | 6/2004 | Moskoff | 436/125 |
| 6,874,355 | B2 * | 4/2005 | Kornfeldt et al. | 73/64.42 |
| 6,925,895 | B2 | 8/2005 | Barker | |
| 7,002,682 | B2 * | 2/2006 | Girvin et al. | 356/335 |
| 7,024,950 | B2 * | 4/2006 | Guldi et al. | 73/863.01 |
| 7,293,473 | B2 * | 11/2007 | Craig et al. | 73/863.01 |
| 2002/0062701 | A1 * | 5/2002 | Guldi et al. | 73/863.23 |
| 2002/0130069 | A1 * | 9/2002 | Moskoff | 210/85 |
| 2003/0061868 | A1 * | 4/2003 | Povey et al. | 73/61.75 |
| 2004/0165185 | A1 * | 8/2004 | Reintjes et al. | 356/335 |
| 2005/0016929 | A1 | 1/2005 | Kashkoush | |
| 2005/0109112 | A1 * | 5/2005 | Gysling et al. | 73/587 |
| 2006/0225522 | A1 * | 10/2006 | Craig et al. | 73/863.01 |
| 2007/0090059 | A1 | 4/2007 | Plummer et al. | |
| 2008/0087076 | A1 * | 4/2008 | Busch | 73/61.71 |

FOREIGN PATENT DOCUMENTS

| | | |
|---|---|---|
| WO | 2005022145 | 3/2005 |
| WO | 2008243399 | 2/2008 |

* cited by examiner

METHOD FOR MONITORING WATER QUALITY

PRIOR APPLICATION

This application is a U.S. national phase application based on International Application No. PCT/US2006/060760, filed 10 Nov. 2006, claiming priority from U.S. Provisional Patent Application No. 60/736,343, filed 14 Nov. 2005.

TECHNICAL FIELD

The method of the present invention is for monitoring water quality in a water system. An on-line method to capture water samples in real time when the water quality deteriorate or contaminates. More particularly, a particle sensor device senses or counts particles. This is the event that may trigger further analysis of the water.

BACKGROUND OF INVENTION

The currently available water quality monitoring systems are quite ineffective since they often measure the water quality at predetermined time intervals such as several times a day, once a week or once in a month. This means the actual testing may occur long after pollutants and other undesirable particles are already in the water flow on their way to the consumers. One problem is that the timing of the testing is not directly correlated to the actual event of the occurrence of the undesirable particles in the water flow. Another problem is that various micro-organisms and bacteria are of about the same size as other harmless microscopic particles in the water which makes it difficult to filter out such microorganisms and bacteria. There is a need for a method that effectively monitors the water quality and automatically collects the desired sample volume for further analyze when water quality/cleanness deteriorates.

SUMMARY OF INVENTION

The method of the present invention provides a solution to the above-outlined problems. More particularly, the method of the present invention is designed so that the testing and analysis of the water quality is event driven based on a continuous sensing or particle count of the water. The system has an on-line automatic microprocessor based testing system that is associated with a refrigerator or another cooled space. Regarding the water system of the present invention, a water pipe is provided for conveying water therein. A particle sensor is in operative engagement with the water pipe. The particle sensor continuously counts particles and classified in different fractions according to their sizes or size distribution in the water of the water pipe. The particle sensor triggers a taking of a water sample only when a particle count reaches a predetermined level of any of particles size and concentration.

DETAILED DESCRIPTION

Figure 1:
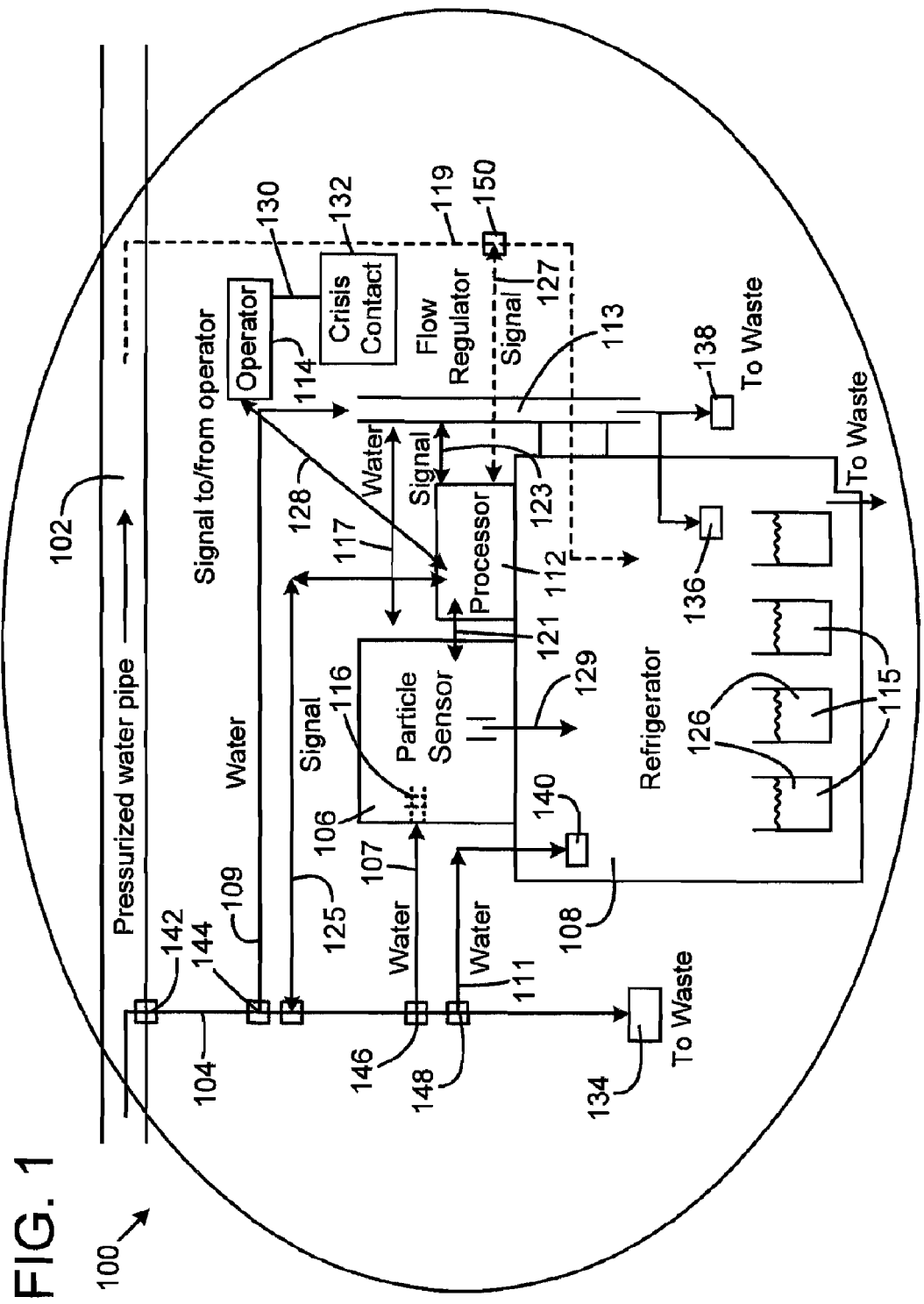
FIG. 1 is a schematic view of the monitoring system of the present invention.

FIG. 1 shows one embodiment of the water monitoring system 100 of the present invention. The system 100 has a pressurized water pipe 102 and a first diverting pipe 104 and a second diverting pipe 119 in fluid communication therewith. The monitoring system of the present invention may be used for both treated and un-treated water. A particle sensor 106 is in operative engagement with the water pipe 102 via a pipe segment 107 to continuously counts and determines size of microscopic particles 116 that flow in the water. Thanks to the two diverting pipes 104 and 119 it is possible to take water samples upstream and downstream of the particle sensor 106. In this way, it is possible to smooth out any variations that may occur in the water samples taken.

Undesirable particles in the water may include, for example, microorganisms, bacteria and parasites such as Cryptosporidium and Giardia or other organic contamination. The particles may also be indications of chemical and radioactive contamination. Bacteria are often in the range of 0.5-10 micrometers, Cryptosporidium 2-7 micrometers and Giardia particles are often in the range of 7-20 micrometers.

The diverting pipe 104 also has a first branch pipe 109 and a second branch pipe 111 connected thereto. The branch pipe 109 is in fluid communication with a flow regulator 113 and the branch pipe 111 is in direct communication with a cooled device or a refrigerator 108 that contains a plurality of containers 115 for storing water samples 126. The containers may store water from 0.1 liter to 100 liter. Of course, the containers may be used to store any suitable amount of water such as 1-2 liters.

In this way, it is possible to analyze water that has not passed through the particle sensor 106. A pipe 117 extends between the particle sensor 106 and the flow regulator 113. One function of the flow regulator is to more accurately set the flow of water by creating a water pillar to ensure that the correct amount of water enters the particle sensor 106 via the pipe 117. The regulator 113 may also be used to remove undesirable air bubbles from the water before the water enters the particle sensor 106. The mechanical flow controller can be replaced by an electronic flow controller.

An important feature of the present invention is the realization of the strong connection between the amount of microscopic particles and the quality of the water because many of the microscopic particles carry contaminants. The particle sensor 106 may be used to count particles both from water conveyed in the pipe 107 and water that has passed through the water regulator 113 and then through the pipe 117 and/or 119.

As indicated earlier, water may be diverted from the water pipe 102 via a second diverting pipe 119 and directly into the refrigerator 108. In this way, it is possible to analyze downstream water that has not passed through the particle sensor 106 and possibilities will be there to connect via the flow regulator 113. These water samples may then be compared to water samples that come from the particle sensor 106 via the pipe 129. As indicated earlier, the device 106 automatically produces water samples, for storage in the refrigerator, when the particle count reaches certain critical values.

The device 106 may count particles using a light scattering technique, light extinction technique or any other suitable technique for counting particles in flowing water. The device 106 may be set to register particles in the range of 0.1-500 micrometers, more preferably in the range of 0.5-100 micrometers. Preferably, the device 106 may classify the particles in the following size ranges: 0.5-1 micrometers, 1-2 micrometers, 2-7 micrometers, 7-20 micrometers and 20-100 micrometers. Of course, the device may be set to classify other suitable size ranges. Most preferably, the device 106 counts particles in the size range of 1-25 micrometers which includes most if not all bacteria and other microorganisms of particular interest for water quality monitoring.

A microprocessor 112, such as a programmable logic configuration (PLC) device, is in operative engagement with the counting device 106, the flow regulator 113, the diverting pipe 104 and the second diverting pipe 119 via signal connections 121, 123, 125 and 127, respectively, to open and close valves connected to the counting device 106, the flow regulator 113 and the water pipes 104, 119 of the water system 100. The microprocessor 112 is in communication with an operator 114 of the water monitoring system 100. The signal 125 may control valves 142, 144, 146, 148. The signal 127 may control the valve 150 of the second diverting pipe 119. The signals 121, 123 control the flow of water in the pipe 117. The microprocessor may store all the particle counts for further analysis.

In operation, the particle sensor 106 continuously counts particles 116 that flow in the water pipes.

When the particle count reaches a critical value over a time period, such as well over 50 particles/ml, an alert or water-testing signal 128 is triggered. In general, the particle count should not exceed 20%, or more preferably 10%, more than the normal base count of particles in the water flow. The particle sensor 106 automatically obtains a water sample 126 for further testing and analysis by the operator 114. The diverting pipe may be connected to a valve to divert water from the main water pipe 102 in order to obtain the water sample 126. The processor may be programmable to arrange for different testing volumes of water. The water samples 126 are preferably automatically kept in the refrigerator 108 to prevent further contamination. As indicated above, the microprocessor 112 activates valves so that a predetermined testing volume of the water sample flows into the containers 115 disposed in the refrigerator 108. The operator 114 may then analyze the water samples 126 in the containers 115. All the events are continuously logged in the processor and/or monitor and/or USB memory and/or flash card.

The alert signal 128 may also be sent to the operator 114 of the water plant. If the particle count reaches a crisis value then a crisis signal 130 may be sent to a crisis contact 132. However, to avoid unnecessary panic, the crisis signal 130 may only be sent after a water test of a sample confirms the very high contamination.

The water may be further analyzed by taking additional water samples such as at locations 134, 136, 138, 140 or any other suitable location. The operator may first do a quick analysis to check the water for cloudiness, color, chlorine, pH, transparency, conductivity, coliform, E-coli or any other suitable parameter. The operator may also check to make sure the rise in particle count is not the result of an internal problem within the water plant itself before an alarm signal is sent out externally.

Figure 2:
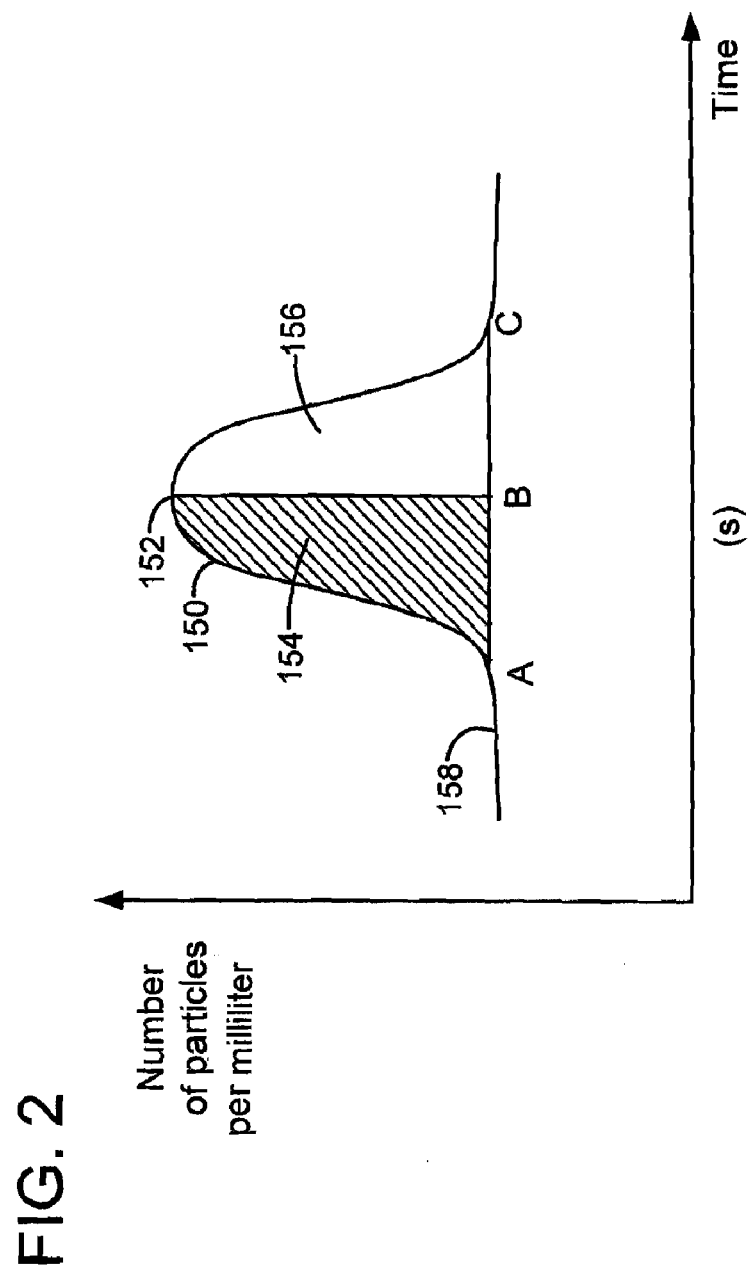
FIG. 2 is a schematic view of graph showing number of particles over a time period.

As shown in FIG. 2, the particle count may gradually increase as shown by the graph 150 and reach a peak value 152 relative to a normal base value 158 of the particle count and then decline. The graph 150 may be designed to show all particles sizes and/or only particles predefined particle size ranges such as 0.5-1 micrometers, 1-2 micrometers, 2-7 micrometers and 7-20 micrometers. By classifying the particle count into size ranges the operator may obtain information about which microorganism type might have contaminated the water. Water testing prior to reaching the peak value 152 may be considered as primary testing 154 and testing subsequent to the peak value may be considered secondary testing 156. One object of the primary testing 154 is to trigger the water testing procedure and alerting the necessary personnel. One purpose of the secondary testing 156 is to make sure no additional peak values or substantial increase in the particle count is occurring.

The particle sensor could be placed anywhere in the process where it is necessary to control the water quality. Another reason for placing the particle sensor in a suitable place is because bio-film may get loosened from the water pipes to contaminate the water. It is therefore very important to capture the water sample at that point.

Figure 3:
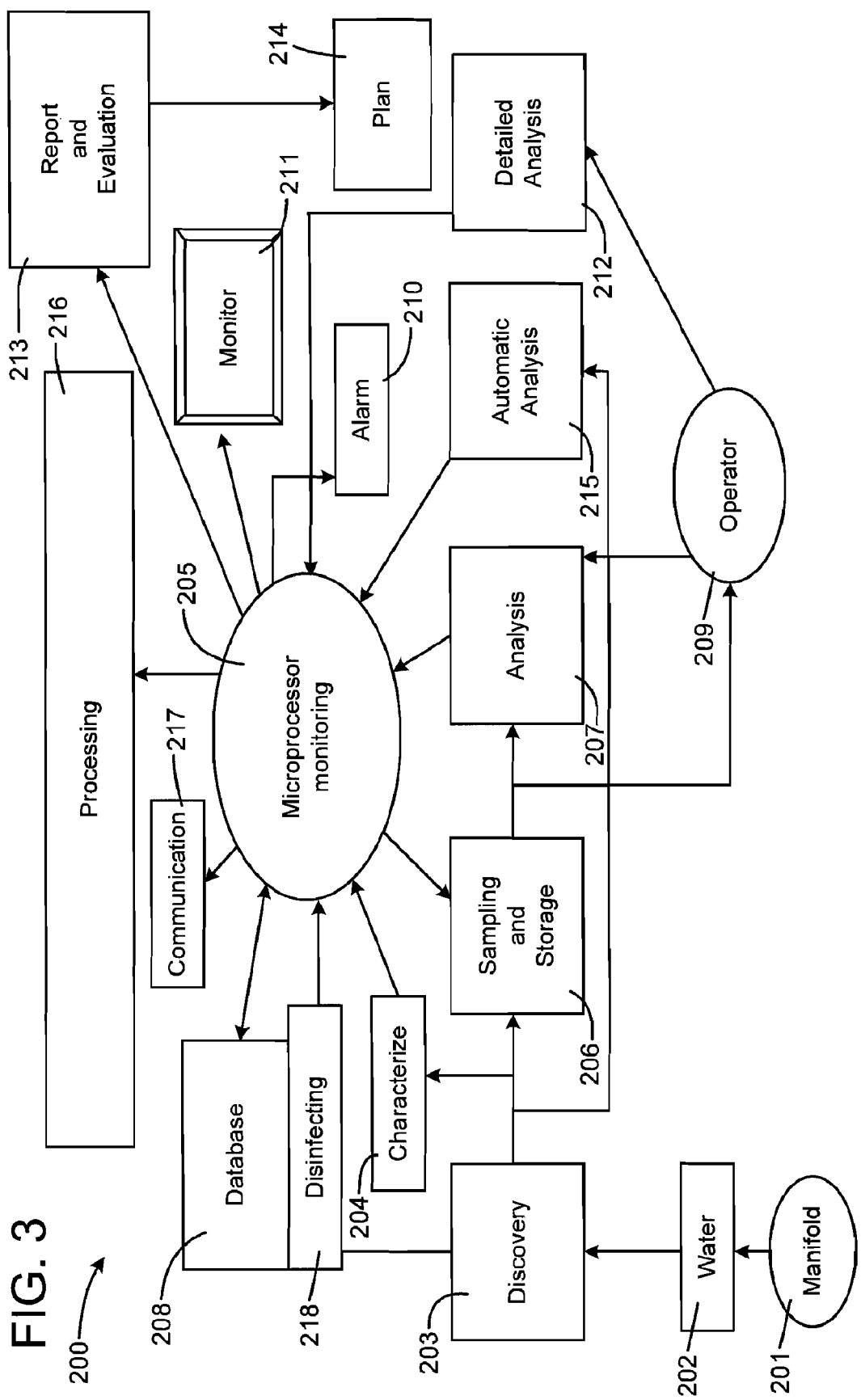
FIG. 3 is a schematic view of the system of the present invention.

With reference to FIG. 3, a system 200 of an embodiment of the present invention is shown. Water 202 to be tested is conveyed via the manifold 201 into a discovery device 203 for discovering or sensing contamination of the water with a particle sensor. It is possible to convey water into the system from various points and the system may include reference water i.e. water that is not contaminated. The water is characterized in a characterizing device 204 and information is sent to a microprocessor monitor 205. The current quality status of the water may be shown in a monitor 211. The microprocessor 205 may evaluate and compare the analysis with information stored in an internal or external database 208. If the analysis determines that a sample should be taken, information from the microprocessor 205 is sent to the sampling and storage device 206 for carrying out water sampling. At the same time, the microprocessor 205 sends instructions to the operator 209 that water samples have been taken and the operator 209 sends confirmation to the microprocessor that the message has been received. The operator 209 then carries out a manual quick analysis 207. The quick analysis 207 may include analysis related to pH, transparency, conductivity, chlorine, color, bacteria, heavy metals, oxygen, temperature, ORP, identification of micro-organisms with PCR technology, TOC, TON, PyGC/MS, UV-VIS and other suitable test parameters. The results are sent to the microprocessor 205 for evaluation with the assistance of the database 208. The information is thereafter sent to the operator 209 that decides whether a detailed laboratory analysis 212 should be carried out. The analysis 212 may include analysis of parameters related to bacteria, parasites, organic substances and other suitable parameters. The operator 209 may then inform a risk management group 214 that a sample has been taken and sent away for detailed laboratory analysis 212. The result of the detailed analysis 212 is sent to the microprocessor 205 for evaluation with the assistance of information stored in the database 208. A signal is sent to a report and evaluation unit 213 and the microprocessor 205 provides suggestions to the risk management group 214 regarding steps to be taken. When the contamination is severe, it is possible to quickly trigger an ozone desinfecting unit 218 to treat the contaminated water with an ozone desinfecting treatment. Alarms of an alarm unit 210 for different levels and risks may be sent by the microprocessor 205 to the operator 209 and the risk management 214. It is possible to obtain information from the microprocessor 205 and the database 208 via a communication device 217 that may include GSM, satellite, Internet or any other suitable communication device or technology. It is also possible to periodically activate or on-line activation of a processing unit 216 for cleaning with automatic flushing, desinfecting, calibration control, validation, sensitivity/precision evaluation, maintenance of the sensor 203 and of the sampling and storage unit 206. As an option, it is also possible to include other on-line measuring instruments 215 for an automatic on-site analysis that may be carried out or be located at the customer or in the system 100. The automatic analysis in the instrument 215 may include analysis of parameters such as image-recognition, cell counter with automatic microscopic observation, TOC/COD, DNA identification, Colifast, toxicity, radioactivity and UV-VIS.

While the present invention has been described in accordance with preferred compositions and embodiments, it is to be understood that certain substitutions and alterations may be made thereto without departing from the spirit and scope of the following claims.

The invention claimed is:

1. A method for monitoring water quality in a water system, comprising:
   providing a pipe for conveying water therein, a particle sensor in operative engagement with the pipe;
   the particle sensor continuously counting particles within a predetermined particle size interval in the water of the pipe;
   the predetermined size interval being a size interval of a microorganism;
   the particle sensor triggering a taking of a sample only when a value of counted particles within the predetermined size interval reaches a predetermined level; and
   performing at least one chemical or microbiological analysis of the water sample.

2. The method according to claim 1 wherein the method further comprises diverting water to a flow regulator and then to the particle sensor to count particles.

3. The method according to claim 1 wherein the method further comprises the particle sensor automatically taking the water sample when the particle count within the predetermined size interval reaches the predetermined level and storing the water sample in a refrigerator.

4. The method according to claim 1, wherein the water sample is analyzed with respect to pH, transparency, conductivity, chlorine, color, bacteria, heavy metals, oxygen, temperature, oxidation-reduction potential (ORP), presence of microorganisms, total organic carbon (TOC) and total organic nitrogen (TON).

5. The method according to claim 1 wherein the method further comprises diverting water in a pipe directly from the water pipe into a refrigerator without passing through the particle sensor.

6. The method according to claim 1 wherein the method further comprises diverting water in a downstream pipe directly into a refrigerator without passing through a flow regulator.

7. The method according to claim 1 wherein the method further comprises sending a crisis signal to a crisis contact.

8. The method according to claim 1 wherein the method further comprises taking the sample when a particle count within the predetermined size interval has reached a peak value.

9. The method according to claim 1, wherein the microorganism is selected from a bacterium or a parasite.

10. The method according to claim 1 wherein the predetermined size interval is within a range of 0.1 micrometer to 25 micrometers.

11. The method according to claim 1 wherein the predetermined size interval is within a range of 0.5 micrometer to 25 micrometers.

12. The method according to claim 1 wherein the predetermined size interval is within a range of 1 micrometer to 25 micrometers.

13. The method according to claim 1 wherein the particle sensor counts particles in several predetermined size intervals.

14. The method according to claim 1 wherein a size distribution of particles in the water of the pipe is determined.

15. The method according to claim 1 wherein the method further comprises the particle sensor triggering a processor to open and close valves.

16. The method according to claim 15 wherein the method further comprises the processor sending an alert signal to an operator only when the particle count within the predetermined size interval has reached the predetermined level.

17. A method for monitoring water quality in a water system, comprising:
   providing a pipe for conveying water therein and a particle sensor in operative engagement with the pipe;
   the particle sensor continuously counting and measuring sizes of particles in the water to continuously provide information about a size distribution of the particles, and
   the particle sensor triggering a taking of a sample and performing at least one chemical or microbiological analysis of the water sample only when a value of counted particles within a predetermined size interval is reached wherein the predetermined size interval is a size interval of a microorganism.

18. The method according to claim 17, wherein the microorganism is selected from a bacterium or a parasite.

* * * * *